United States Patent [19]

Morales-George

[11] Patent Number: 4,654,032
[45] Date of Patent: Mar. 31, 1987

[54] DRAINAGE "T" TUBE USED FOR ABDOMINAL SURGERY

[76] Inventor: Hector Morales-George, 1170 SW. 102 Ave., Miami, Fla. 33174

[21] Appl. No.: 864,750

[22] Filed: May 13, 1986

Related U.S. Application Data

[63] Continuation of Ser. No. 623,341, Jun. 22, 1984.

[51] Int. Cl.$^4$ ............................................. A61M 5/00
[52] U.S. Cl. ..................................... 604/174; 604/284
[58] Field of Search ............................. 604/174–180, 604/280–283, 284; 128/DIG. 26

[56] References Cited

U.S. PATENT DOCUMENTS

| | | | |
|---|---|---|---|
| 2,898,917 | 8/1959 | Wallace | 604/180 |
| 3,663,965 | 5/1972 | Lee, Jr. et al. | 604/175 |
| 3,835,863 | 9/1974 | Goldberg et al. | 604/284 |
| 3,881,199 | 5/1975 | Treace | 604/280 X |
| 4,080,970 | 3/1978 | Miller | 604/174 |
| 4,142,528 | 3/1979 | Whelan | 604/284 |
| 4,435,174 | 3/1984 | Redmond et al. | 604/174 |

Primary Examiner—Stephen C. Pellegrino
Attorney, Agent, or Firm—Robert T. Gammons

[57] ABSTRACT

A catheter in the form of a flexible T tube for insertion of an end thereof through a natural or incised opening in the body of sufficient length to extend from said opening and an anchoring member attached to the stem of the T tube containing openings for receiving suturing for attaching the anchoring member to the skin at the place of entry of the stem into the opening.

1 Claim, 5 Drawing Figures

DRAINAGE "T" TUBE USED FOR ABDOMINAL SURGERY

This is a continuation of co-pending application Ser. No. 623,341 filed on June 22, 1984.

BACKGROUND OF THE INVENTION

Catheters in the form of flexible tubes of a length to be inserted through a natural or incised opening in the body for introduction of fluids into the body or for drainage of fluids from the body are well known. Most such tubes are held in place by adhesive tape or its equivalent. However, since the tube is generally comprised of rubber or plastic, the tape does not always adhere securely and, further, since it is exposed to abrasive contact of clothing and/or bedding, it can be loosened by a restless patient. Without some means of securing the tube in place, there is always the risk that the patient, willingly or unwillingly, or some other person, may pull the tube out with serious consequences. It is the purpose of this invention to provide an improved catheter as, for example, a T tube structured to prevent inadvertent or purposeful withdrawal of the tube.

SUMMARY OF THE INVENTION

As herein illustrated, the invention resides in providing a catheter designed for insertion through a natural or incised opening in the body of the patient to be treated and comprising a flexible tube of such length as to extend from the exterior of the body through the opening into the body with means secured to the exterior of the tube intermediate its ends by means of which the tube can be attached by suturing to the skin of the patient in the area where the tube enters the body to prevent accidental or purposeful displacement of the tube. The catheter may be of the type known as a T tube in biliary tract surgery comprising a stem and cross head. The anchoring member comprises a thin, flat flange positioned about the axis of the stem in a plane at right angles thereto and is desirably symmetrically configured with respect to the axis of the stem. The flange may be formed integral with the stem of the tube. To provide for attachment, the flange is provided with peripherally-spaced openings for receiving a suture.

The invention will now be described in greater detail with reference to the accompanying drawings, wherein.

Figure 1:
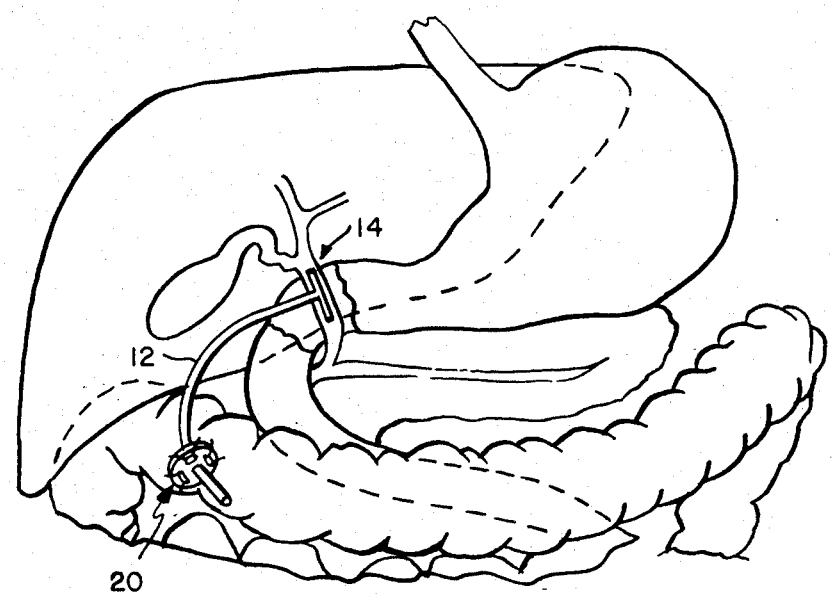
FIG. 1 represents a typical use of the device of this invention placed in an abdominal cavity and secured in place by stitching to the skin of the patient at the place of entry of the tube.
Figure 3:
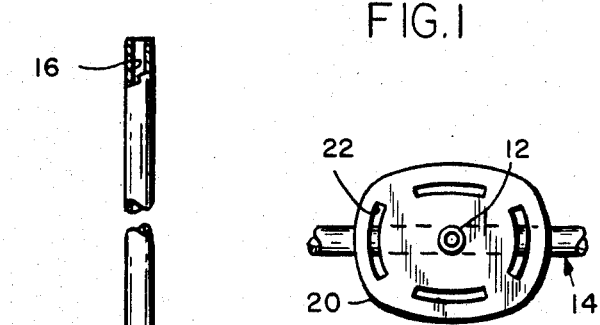
FIG. 3 is a section taken on the line 3—3 of FIG. 2 showing the anchoring means in elevation.
Figure 2:
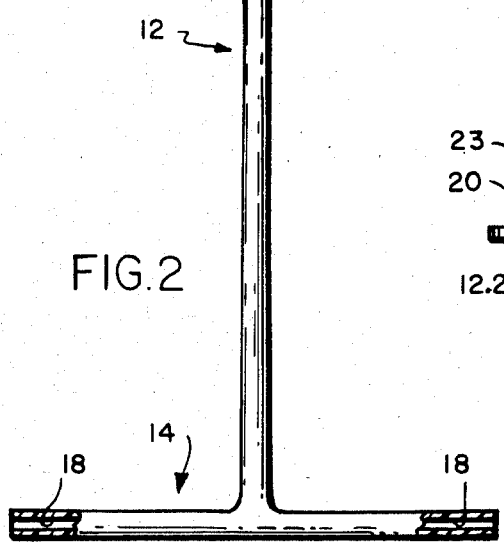
FIG. 2 is a plan view of the catheter in the form of a T tube used for abdominal surgery biliary tact (common duct) provided with the improved anchoring means of this invention for attaching the catheter to the abdominal wall of the patient.
Figure 4:
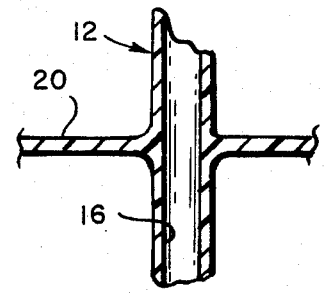
FIG. 4 is a fragmentary section taken on the axis of the T tube at the junction of the anchoring means therewith.

Referring to the drawings, FIG. 1, there is shown a typical use of the improved catheter of this invention in the form of a T tube implanted in an abdominal cavity common duct (biliary tract surgery) and secured therein by the attaching or anchoring means of the instant invention. The T tube in one form, as shown in FIGS. 2, 3 and 4, is formed of flexible rubber or plastic and comprises a stem 12 and a cross head 14 common duct biliary tract surgery which define a longitudinal passage 16 and transverse passages 18—18. As shown in FIG. 1, the T tube is implanted with the cross head 14 within the cavity or passage to be treated and the stem 12 extending therefrom through a natural or incised opening to the exterior to conduct fluid to or from the cavity. In this form of the invention, that is, as illustrated in FIGS. 2, 3 and 4, the diameter of the tubing of which the T tube is comprised is approximately 0.218 inches. The length of the stem is approximately 12.5 inches and the length of the head is approximately 4.875 inches.

In accordance with the invention, to secure the T tube in its emplaced position so that it cannot be accidentally or purposely removed without authorization, anchoring means in the form of a flange 20 is employed. The flange 20 is of generally oval configuration, as shown in FIG. 3, is applied to the stem 12 of the T tube intermediate its ends, and is symmetrical with respect to the axis of the stem. Symmetrically-positioned slots 22 are formed through the flange through which sutures S can be sewn to attach the flange to the abdominal wall about the opening from which the free end of the stem extends. As herein shown, the flange is approximately 1.58 inches across its long dimension, approximately 1.54 inches across its short dimension and approximately 0.10 inches in thickness. In the form shown in FIGS. 2, 3 and 4, the flange is formed integral with the wall of the stem and while shown to be of oval configuration, it can be of circular, rectangular or triangular configuration. Furthermore, while the plane of the flange is illustrated at right angles to the axis of the stem, it can be, for appropriate use, inclined to the axis of the stem.

Figure 5:
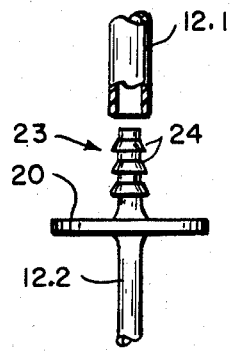
FIG. 5 is a plan view of a modification of the T tube in which portions of the T tube are separable adjacent the anchoring means.

An alternative form of the T tube embodying the invention is shown in FIG. 5 wherein the stem 12 is divided intermediate its ends into lengths 12.1 and 12.2. The section 12.2 is connected at one end to the cross head 14 and has at its opposite end the flange 20 and coupling means 23 for coupling it to the length 12.1. The coupling means 23 comprises a nipple provided with a plurality of frustoconically-shaped ribs 24 adapted to be force-fitted into the length 12.1. In this instance, the length 12.2 which embodies the cross head 14, the flange 20 and the coupling means 23 is approximately 5.90 inches. In other respects, the diameter of the stem and the cross head are the same as in FIG. 2.

The several forms of the invention as described above are illustrated for use in surgery in conjunction with drainage of abdomincal cavities. However, it is to be understood that the T tube structured according to this invention with anchoring means can be used for other purposes, for example, introducing fluid into a cavity or organ or blood vessel. Further, while the catheter described is a T tube, the same anchoring member employed to secure the stem in place can also be employed for securing a catheter in the form of a straight tube without a cross head. The flange 20 could be employed, for example, in conjunction with the surgical drain shown in U.S. Pat. No. 2,618,271 by applying it to the stem thereof.

It is to be understood that it is within the scope of the invention to form the tube, whether a T tube or a straight tube, and the flange of any suitable flexible material, to employ a flange of circular, rectangular or triangular configuration, and to dispose the flange in a plane inclined at an angle to the axis of the stem of the tube for such purposes as would require such angular disposition of the flange relative to the axis of the tube.

It should be understood that the present disclosure is for the purpose of illustration only and includes all modifications or improvements which fall within the scope of the appended claims.

What is claimed is:

1. The combination with a T tube embodying a tubular leg, at one end of which there is a tubular cross arm disposed at right angles to the tublar leg, said composite structure being designed for surgical drainage; of improve attaching means for attaching the T tube to the skin of the patient following implantation of the tube through a natural or incised opening in the body of the patient, comprising a flake adapted to be attached to the exterior surface of skin bounding the opening, said flake being disposed at right angles to the axis of the tubular leg and parallel to the aixs of the tubular cross arm formed integral with the leg of the T tube at a predetermined distance from the cross arm, said flake being symmetrical with respect to the longitudinal axis of the tubular leg and of generally elliptical configuration defining spaced, parellel, flat faces, spaced, parallel, rectilinear end edges and spaced, opposed, arcuate side edges, so disposed that said end edges are at predetermined equal distances from the axis of the leg, the side edges are at preetermined shorter distance from the axis of the leg and the planes of said flat faces are at right angles to the axis of the leg, wherein the end edges are parallel to the axis of the cross arm, and the side edges are transverse thereto and wherein the flake contains elongate, relatively narrow, rectangular openings parallel to its end edges, spaced from said end edges at equal radial distances and from the axis of the leg at distance greater than the distances of the openings from the end edges for receiving a suture for attaching the flake to the skin at the place of entry of the tube into the opening.

* * * * *